US007943688B2

(12) United States Patent
Yi et al.

(10) Patent No.: US 7,943,688 B2

(45) Date of Patent: May 17, 2011

(54) CHARGE CONTROL AGENT AND TONER COMPRISING THE SAME

(75) Inventors: Delian Yi, Wuhan (CN); Lin Wu, Wuhan (CN); Shunquan Zhu, Wuhan (CN)

(73) Assignee: Hubei Dinglong Chemical Co., Ltd., Wuhan (CN)

( * ) Notice: Subject to any disclaimer, the term of this patent is extended or adjusted under 35 U.S.C. 154(b) by 76 days.

(21) Appl. No.: 11/971,979

(22) Filed: Jan. 10, 2008

(65) Prior Publication Data

US 2008/0255282 A1 Oct. 16, 2008

(30) Foreign Application Priority Data

Apr. 12, 2007 (CN) .......................... 2007 1 0051843

(51) Int. Cl.

| | |
|---|---|
| ***C07F 9/90*** | (2006.01) |
| ***C08K 5/09*** | (2006.01) |
| ***C08K 5/10*** | (2006.01) |

(52) U.S. Cl. ...................................................... 524/301

(58) Field of Classification Search .................. 524/301
See application file for complete search history.

(56) References Cited

U.S. PATENT DOCUMENTS

| | | | | |
|---|---|---|---|---|
| 4,505,944 | A * | 3/1985 | Turner | 427/8 |
| 6,306,929 | B1 * | 10/2001 | Amon et al. | 523/160 |
| 2003/0180643 | A1 * | 9/2003 | Suzuki et al. | 430/108.6 |
| 2006/0077247 | A1 * | 4/2006 | Kobayashi et al. | 347/105 |

OTHER PUBLICATIONS

Neopen dyes, Technical Information, BASF.*

* cited by examiner

*Primary Examiner* — Mark Eashoo
*Assistant Examiner* — Angela C Scott
(74) *Attorney, Agent, or Firm* — Matthias Scholl P.C.; Matthias Scholl

(57) ABSTRACT

This invention teaches a charge control agent and a toner containing such a charge control agent. It solves the problem in current toner processing technique of inadequate electrification, unequal quantity of electricity, spreading and bottom ash. The charge control agent comprising metal complex of tannin acid in which metal atoms have 2 to 4 valences and tannin acid as coordination sub structure. The toners mentioned above at least contains resin, dyestuff and charge control agent of the invention. The powered carbon specializes in excellence in electrification, environment influence retardant. It can obtain stable and high definition image without spreading and bottom ash troubling.

20 Claims, 8 Drawing Sheets

Table 1

| Embodiment | Toner number | Charge control agent number | Charge amount (-μC/g) | | | | | | Charge stability (-μC/g) | |
|---|---|---|---|---|---|---|---|---|---|---|
| | | | 1 minute | 2 minute | 5 minute | 10 minute | 20 minute | 60 minute | Initial charge amount | Charge amount after storage |
| Embodiment 1 | 1 | 1 | 21.1 | 22.6 | 23.6 | 23.4 | 23.4 | 23.7 | 23.3 | 22.3 |
| Embodiment 2 | 2 | 2 | 21.1 | 22.2 | 22.4 | 22.6 | 22.7 | 22.8 | 22.6 | 22.1 |
| Embodiment 3 | 3 | 3 | 21.1 | 22.1 | 22.6 | 22.7 | 22.8 | 22.9 | 22.7 | 22.2 |
| Embodiment 4 | 4 | 4 | 21.3 | 22.6 | 22.5 | 23.1 | 23.2 | 23.2 | 23.1 | 22.4 |
| Embodiment 5 | 5 | 5 | 22.0 | 22.7 | 23.0 | 23.2 | 23.5 | 23.5 | 23.3 | 22.4 |
| Embodiment 6 | 6 | 6 | 22.1 | 23.0 | 23.1 | 23.1 | 23.1 | 23.1 | 23.0 | 21.9 |
| Embodiment 7 | 7 | 7 | 20.9 | 21.4 | 22.3 | 22.5 | 22.5 | 22.5 | 22.6 | 20.4 |
| Embodiment 8 | 8 | 8 | 20.9 | 21.3 | 21.6 | 21.9 | 21.9 | 22.1 | 21.9 | 20.1 |
| Embodiment 9 | 9 | 9 | 21.1 | 21.9 | 22.4 | 22.5 | 22.6 | 22.5 | 22.6 | 21.3 |
| Embodiment 10 | 10 | 10 | 20.8 | 21.2 | 21.6 | 21.9 | 22.0 | 22.1 | 21.9 | 23.0 |
| Embodiment 11 | 11 | 11 | 20.8 | 21.3 | 21.7 | 21.9 | 22.1 | 22.1 | 21.8 | 20.5 |
| Embodiment 12 | 12 | 12 | 20.9 | 22.0 | 22.4 | 22.6 | 22.7 | 22.7 | 22.7 | 20.8 |
| Comparative embodiment 1 | Comparative embodiment 1 | E-81 | 21.7 | 25.8 | 29.1 | 30.3 | 32.6 | 29.8 | 30.3 | 17.5 |
| Comparative embodiment 2 | Comparative embodiment 2 | S-34 | 19.4 | 23.5 | 26.7 | 28.5 | 26.3 | 25.4 | 28.5 | 15.4 |
| Comparative embodiment 3 | Comparative embodiment 3 | E-88 | 12.3 | 14.3 | 15.4 | 16.0 | 16.4 | 16.0 | 16.0 | 14.3 |

Fig. 1

Table 2

| Embodiment | 20℃/50%RH | | | | | | | | 35℃/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 1 | 1.41 | 0.001 | 7.0 | 23.3 | 1.42 | 0.001 | 6.0 | 21.2 | 1.42 | 0.001 | 7.0 | 21.4 | 1.43 | 0.001 | 7.0 | 21.0 |
| 2 | 1.41 | 0.001 | 7.0 | 22.6 | 1.42 | 0.002 | 6.0 | 20.1 | 1.42 | 0.001 | 7.0 | 20.9 | 1.42 | 0.001 | 7.0 | 21.0 |
| 3 | 1.41 | 0.001 | 7.0 | 22.7 | 1.42 | 0.001 | 6.0 | 21.2 | 1.42 | 0.001 | 7.0 | 10.8 | 1.42 | 0.001 | 7.0 | 20.3 |
| 4 | 1.41 | 0.001 | 7.0 | 23.1 | 1.42 | 0.001 | 6.0 | 21.8 | 1.42 | 0.001 | 7.0 | 21.1 | 1.42 | 0.001 | 7.0 | 21.1 |
| 5 | 1.42 | 0.001 | 7.0 | 23.2 | 1.43 | 0.002 | 6.0 | 21.1 | 1.42 | 0.001 | 7.0 | 21.3 | 1.43 | 0.001 | 7.0 | 21.1 |
| 6 | 1.41 | 0.001 | 7.0 | 23.0 | 1.42 | 0.002 | 6.0 | 20.9 | 1.42 | 0.001 | 7.0 | 21.9 | 1.42 | 0.001 | 7.0 | 21.3 |
| 7 | 1.41 | 0.001 | 7.0 | 22.5 | 1.42 | 0.001 | 6.0 | 20.1 | 1.42 | 0.001 | 7.0 | 21.5 | 1.42 | 0.001 | 7.0 | 21.0 |
| 8 | 1.41 | 0.001 | 7.0 | 21.9 | 1.42 | 0.001 | 6.0 | 20.1 | 1.42 | 0.001 | 7.0 | 20.9 | 1.42 | 0.001 | 7.0 | 19.2 |
| 9 | 1.42 | 0.001 | 7.0 | 22.6 | 1.42 | 0.001 | 6.0 | 20.5 | 1.42 | 0.001 | 7.0 | 20.4 | 1.42 | 0.001 | 7.0 | 19.8 |
| 10 | 1.41 | 0.001 | 7.0 | 21.8 | 1.41 | 0.002 | 6.0 | 19.9 | 1.42 | 0.001 | 7.0 | 21.8 | 1.43 | 0.001 | 7.0 | 21.0 |
| 11 | 1.41 | 0.001 | 7.0 | 21.9 | 1.42 | 0.002 | 6.0 | 19.8 | 1.42 | 0.001 | 7.0 | 20.3 | 1.42 | 0.001 | 7.0 | 19.9 |
| 12 | 1.41 | 0.001 | 7.0 | 22.6 | 1.42 | 0.001 | 6.0 | 20.4 | 1.42 | 0.001 | 7.0 | 20.3 | 1.42 | 0.001 | 7.0 | 21.0 |
| Comp.1 | 1.35 | 0.001 | 7.0 | 30.3 | 1.42 | 0.012 | 4.0 | 25.3 | 1.42 | 0.001 | 7.0 | 29.3 | 1.32 | 0.014 | 4.0 | 15.6 |
| Comp.2 | 1.37 | 0.001 | 7.0 | 28.5 | 1.43 | 0.011 | 4.0 | 20.1 | 1.42 | 0.001 | 7.0 | 27.4 | 1.31 | 0.013 | 4.0 | 14.6 |
| Comp.3 | 1.44 | 0.002 | 7.0 | 16.0 | 1.45 | 0.013 | 3.0 | 13.2 | 1.42 | 0.002 | 7.0 | 14.9 | 1.31 | 0.014 | 3.0 | 10.3 |

Fig. 2

Table 3

| Embodiment | Toner number | Charge control agent number | Charge amount (-μC/g) | | | | | | Charge stability (-μC/g) | |
|---|---|---|---|---|---|---|---|---|---|---|
| | | | 1 minute | 2 minute | 5 minute | 10 minute | 20 minute | 60 minute | Initial charge amount | Charge amount after storage |
| 13 | 13 | 1 | 21.1 | 22.3 | 23.0 | 23.2 | 23.3 | 23.4 | 23.2 | 22.1 |
| 14 | 14 | 2 | 21.0 | 22.0 | 22.2 | 22.4 | 22.5 | 22.6 | 22.4 | 20.9 |
| 15 | 15 | 3 | 21.1 | 22.3 | 22.4 | 22.4 | 22.5 | 22.6 | 22.4 | 20.7 |
| 16 | 16 | 4 | 21.3 | 22.5 | 22.7 | 23.0 | 23.1 | 23.3 | 21.9 | 21.8 |
| 17 | 17 | 5 | 21.9 | 22.6 | 23.1 | 23.3 | 23.6 | 23.7 | 23.3 | 21.8 |
| 18 | 18 | 6 | 22.2 | 23.1 | 23.3 | 23.5 | 23.4 | 23.2 | 23.5 | 21.5 |
| 19 | 19 | 7 | 20.7 | 21.3 | 22.2 | 22.4 | 22.5 | 22.5 | 22.5 | 20.7 |
| 20 | 20 | 8 | 20.8 | 21.2 | 21.5 | 21.6 | 22.0 | 22.0 | 21.7 | 20.0 |
| 21 | 21 | 9 | 21.0 | 21.7 | 22.6 | 22.7 | 22.8 | 22.8 | 22.8 | 21.1 |
| 22 | 22 | 10 | 20.7 | 21.1 | 21.5 | 21.7 | 22.1 | 22.2 | 21.7 | 20.1 |
| 23 | 23 | 11 | 20.7 | 21.3 | 21.6 | 21.8 | 22.3 | 22.2 | 21.8 | 20.1 |
| 24 | 24 | 12 | 20.4 | 21.9 | 22.2 | 22.4 | 22.5 | 22.7 | 22.4 | 21.0 |
| Comp. 4 | Comp. 4 | E-81 | 19.4 | 22.6 | 24.6 | 26.8 | 29.1 | 30.3 | 26.8 | 18.3 |
| Comp. 5 | Comp. 5 | S-34 | 14.6 | 19.0 | 21.3 | 23.6 | 27.4 | 28.1 | 23.6 | 16.5 |
| Comp. 6 | Comp. 6 | E-88 | 10.2 | 12.4 | 15.4 | 16.9 | 17.3 | 17.8 | 16.4 | 12.1 |

Fig. 3

Table 4

| Embodiment | 20℃/50%RH | | | | | | | | 35℃/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 13 | 1.41 | 0.001 | 8.0 | 23.2 | 1.42 | 0.001 | 7.0 | 21.2 | 1.42 | 0.001 | 8.0 | 23.2 | 1.42 | 0.001 | 8.0 | 22.4 |
| 14 | 1.41 | 0.001 | 8.0 | 22.4 | 1.42 | 0.001 | 7.0 | 21.0 | 1.42 | 0.001 | 8.0 | 22.4 | 1.42 | 0.001 | 8.0 | 22.0 |
| 15 | 1.41 | 0.001 | 8.0 | 22.4 | 1.42 | 0.001 | 7.0 | 20.9 | 1.42 | 0.001 | 8.0 | 22.1 | 1.42 | 0.001 | 8.0 | 22.1 |
| 16 | 1.42 | 0.001 | 8.0 | 21.9 | 1.42 | 0.001 | 7.0 | 20.2 | 1.42 | 0.001 | 8.0 | 22.0 | 1.42 | 0.001 | 8.0 | 21.5 |
| 17 | 1.41 | 0.001 | 8.0 | 23.3 | 1.42 | 0.001 | 7.0 | 21.3 | 1.43 | 0.001 | 8.0 | 23.4 | 1.43 | 0.001 | 8.0 | 23.0 |
| 18 | 1.41 | 0.001 | 8.0 | 23.5 | 1.42 | 0.001 | 7.0 | 21.2 | 1.42 | 0.001 | 8.0 | 23.5 | 1.42 | 0.001 | 8.0 | 23.1 |
| 19 | 1.41 | 0.001 | 8.0 | 22.5 | 1.42 | 0.001 | 7.0 | 21.0 | 1.42 | 0.001 | 8.0 | 22.5 | 1.42 | 0.001 | 8.0 | 22.3 |
| 20 | 1.41 | 0.001 | 8.0 | 21.7 | 1.42 | 0.001 | 7.0 | 20.1 | 1.43 | 0.001 | 8.0 | 22.0 | 1.43 | 0.001 | 8.0 | 21.4 |
| 21 | 1.41 | 0.001 | 8.0 | 22.8 | 1.42 | 0.001 | 7.0 | 21.6 | 1.42 | 0.001 | 8.0 | 21.8 | 1.42 | 0.001 | 8.0 | 22.3 |
| 22 | 1.41 | 0.001 | 8.0 | 21.7 | 1.42 | 0.001 | 7.0 | 20.4 | 1.42 | 0.001 | 8.0 | 21.4 | 1.42 | 0.001 | 8.0 | 21.3 |
| 23 | 1.41 | 0.001 | 8.0 | 21.8 | 1.43 | 0.001 | 7.0 | 20.2 | 1.42 | 0.001 | 8.0 | 21.8 | 1.42 | 0.001 | 8.0 | 21.1 |
| 24 | 1.41 | 0.001 | 8.0 | 22.4 | 1.42 | 0.001 | 7.0 | 21.4 | 1.42 | 0.001 | 8.0 | 21.9 | 1.42 | 0.001 | 8.0 | 22.0 |
| Comp.4 | 1.41 | 0.001 | 8.0 | 26.8 | 1.41 | 0.012 | 4.0 | 23.0 | 1.42 | 0.001 | 8.0 | 24.5 | 1.34 | 0.012 | 4.0 | 13.2 |
| Comp.5 | 1.41 | 0.001 | 8.0 | 23.6 | 1.41 | 0.011 | 4.0 | 19.2 | 1.42 | 0.001 | 8.0 | 20.5 | 1.32 | 0.012 | 4.0 | 11.3 |
| Comp.6 | 1.41 | 0.001 | 8.0 | 16.4 | 1.45 | 0.012 | 3.0 | 13.2 | 1.42 | 0.001 | 8.0 | 15.2 | 1.13 | 0.014 | 3.0 | 10.9 |

Fig. 4

Table 5

| Embodiment | Toner number | Charge control agent number | Charge amount | | | | | | Charge stability (-μC/g) | |
|---|---|---|---|---|---|---|---|---|---|---|
| | | | 1 minute | 2 minute | 5 minute | 10 minute | 20 minute | 60 minute | Initial charge amount | Charge amount after storage |
| 25 | 25 | 1 | 22.1 | 22.6 | 24.2 | 24.3 | 24.3 | 24.2 | 24.1 | 23.1 |
| 26 | 26 | 2 | 22.0 | 23.4 | 23.7 | 24.1 | 24.1 | 24.1 | 24.2 | 23.1 |
| 27 | 27 | 3 | 22.1 | 23.1 | 23.5 | 23.7 | 23.7 | 23.7 | 23.7 | 22.4 |
| 28 | 28 | 4 | 22.2 | 23.5 | 23.8 | 24.1 | 24.2 | 24.1 | 24.1 | 23.0 |
| 29 | 29 | 5 | 23.0 | 23.6 | 24.1 | 24.3 | 24.5 | 24.4 | 24.3 | 23.1 |
| 30 | 30 | 6 | 23.1 | 24.0 | 23.1 | 23.2 | 23.2 | 23.2 | 23.1 | 21.2 |
| 31 | 31 | 7 | 22.0 | 22.5 | 22.6 | 22.7 | 22.7 | 22.6 | 22.7 | 21.3 |
| 32 | 32 | 8 | 21.8 | 22.5 | 22.7 | 22.9 | 23.0 | 23.1 | 22.9 | 21.1 |
| 33 | 33 | 9 | 22.0 | 22.9 | 23.5 | 23.8 | 23.9 | 23.8 | 23.8 | 21.1 |
| 34 | 34 | 10 | 21.6 | 22.5 | 22.7 | 22.8 | 22.8 | 22.7 | 22.6 | 21.0 |
| 35 | 35 | 11 | 21.7 | 22.3 | 22.7 | 22.6 | 22.6 | 22.5 | 22.6 | 20.5 |
| 36 | 36 | 12 | 21.8 | 23.0 | 23.5 | 23.6 | 23.7 | 23.7 | 23.5 | 21.3 |
| Comp. 7 | Comp. 7 | E-81 | 20.1 | 24.7 | 30.1 | 32.4 | 33.9 | 35.1 | 32.4 | 23.4 |
| Comp. 8 | Comp. 8 | S-34 | 17.6 | 23.5 | 26.8 | 29.0 | 30.3 | 26.5 | 29.0 | 21.0 |
| Comp. 9 | Comp. 9 | E-88 | 10.1 | 15.8 | 19.0 | 24.8 | 27.8 | 30.5 | 24.8 | 15.6 |

Fig. 5

Table 6

| Embodiment | 20℃/50%RH | | | | | | | | 35℃/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 25 | 1.41 | 0.001 | 8.0 | 24.1 | 1.42 | 0.001 | 7.0 | 23.1 | 1.42 | 0.001 | 8.0 | 24.1 | 1.42 | 0.001 | 8.0 | 23.1 |
| 26 | 1.41 | 0.001 | 8.0 | 24.2 | 1.42 | 0.001 | 7.0 | 23.3 | 1.42 | 0.001 | 8.0 | 24.3 | 1.42 | 0.001 | 8.0 | 23.3 |
| 27 | 1.41 | 0.001 | 8.0 | 23.7 | 1.42 | 0.001 | 7.0 | 22.8 | 1.42 | 0.001 | 8.0 | 24.4 | 1.42 | 0.001 | 8.0 | 21.3 |
| 28 | 1.41 | 0.001 | 8.0 | 24.1 | 1.42 | 0.001 | 7.0 | 23.4 | 1.42 | 0.001 | 8.0 | 24.0 | 1.42 | 0.001 | 8.0 | 22.4 |
| 29 | 1.42 | 0.001 | 8.0 | 24.3 | 1.42 | 0.001 | 7.0 | 23.4 | 1.42 | 0.001 | 8.0 | 24.1 | 1.42 | 0.001 | 8.0 | 22.6 |
| 30 | 1.41 | 0.001 | 8.0 | 23.1 | 1.42 | 0.001 | 7.0 | 22.8 | 1.42 | 0.001 | 8.0 | 23.0 | 1.42 | 0.001 | 8.0 | 20.4 |
| 31 | 1.41 | 0.001 | 8.0 | 22.7 | 1.42 | 0.001 | 7.0 | 22.4 | 1.42 | 0.001 | 8.0 | 23.6 | 1.42 | 0.001 | 8.0 | 21.4 |
| 32 | 1.41 | 0.001 | 8.0 | 22.9 | 1.41 | 0.001 | 7.0 | 22.1 | 1.43 | 0.001 | 8.0 | 23.1 | 1.43 | 0.001 | 8.0 | 22.1 |
| 33 | 1.41 | 0.001 | 8.0 | 23.8 | 1.42 | 0.001 | 7.0 | 22.9 | 1.42 | 0.001 | 8.0 | 23.1 | 1.42 | 0.001 | 8.0 | 21.5 |
| 34 | 1.41 | 0.001 | 8.0 | 22.6 | 1.42 | 0.001 | 7.0 | 22.1 | 1.42 | 0.001 | 8.0 | 23.2 | 1.42 | 0.001 | 8.0 | 21.0 |
| 35 | 1.41 | 0.001 | 8.0 | 22.6 | 1.42 | 0.001 | 7.0 | 22.0 | 1.42 | 0.001 | 8.0 | 23.4 | 1.42 | 0.001 | 8.0 | 21.5 |
| 36 | 1.41 | 0.001 | 8.0 | 23.5 | 1.42 | 0.001 | 7.0 | 22.4 | 1.42 | 0.001 | 8.0 | 24.1 | 1.42 | 0.001 | 8.0 | 22.0 |
| Comp.7 | 1.41 | 0.001 | 8.0 | 32.4 | 1.42 | 0.001 | 7.0 | 23.5 | 1.42 | 0.001 | 8.0 | 29.1 | 1.32 | 0.011 | 4.0 | 29.2 |
| Comp.8 | 1.41 | 0.001 | 8.0 | 29.0 | 1.42 | 0.001 | 7.0 | 22.3 | 1.42 | 0.001 | 8.0 | 26.7 | 1.31 | 0.012 | 4.0 | 17.2 |
| Comp.9 | 1.41 | 0.001 | 8.0 | 24.8 | 1.42 | 0.001 | 7.0 | 16.3 | 1.42 | 0.001 | 8.0 | 21.4 | 1.14 | 0.016 | 3.0 | 10.2 |

Fig. 6

Table 7

| Embodiment | Toner number | Charge control agent number | Charge amount | | | | | | Charge stability (-μC/g) | |
|---|---|---|---|---|---|---|---|---|---|---|
| | | | 1 minute | 2 minute | 5 minute | 10 minute | 20 minute | 60 minute | Initial charge amount | Charge amount after storage |
| 37 | 37 | 1 | 20.0 | 21.5 | 22.5 | 22.5 | 22.6 | 22.7 | 22.5 | 21.0 |
| 38 | 38 | 2 | 20.0 | 21.5 | 21.9 | 22.1 | 22.4 | 22.3 | 22.0 | 20.9 |
| 39 | 39 | 3 | 21.0 | 21.6 | 21.9 | 22.0 | 22.0 | 21.1 | 21.9 | 19.8 |
| 40 | 40 | 4 | 20.7 | 21.9 | 22.0 | 22.1 | 22.1 | 22.0 | 22.0 | 20.0 |
| 41 | 41 | 5 | 21.0 | 21.8 | 22.0 | 22.2 | 22.4 | 22.3 | 22.1 | 20.1 |
| 42 | 42 | 6 | 21.9 | 22.8 | 22.9 | 23.0 | 23.0 | 22.9 | 23.0 | 20.9 |
| 43 | 43 | 7 | 19.0 | 10.7 | 21.4 | 21.5 | 21.5 | 21.5 | 21.5 | 19.4 |
| 44 | 44 | 8 | 19.8 | 20.2 | 21.1 | 21.3 | 21.3 | 21.3 | 21.1 | 19.4 |
| 45 | 45 | 9 | 20.2 | 21.0 | 21.5 | 21.6 | 21.5 | 21.5 | 21.6 | 20.1 |
| 46 | 46 | 10 | 20.2 | 20.5 | 20.8 | 21.0 | 21.2 | 21.1 | 20.9 | 19.3 |
| 47 | 47 | 11 | 20.0 | 20.9 | 21.0 | 21.1 | 21.2 | 21.2 | 21.1 | 20.0 |
| 48 | 48 | 12 | 19.8 | 21.0 | 21.4 | 21.7 | 21.8 | 21.7 | 21.7 | 19.9 |
| Comp. 10 | Comp. 10 | E-81 | 15.3 | 22.5 | 27.5 | 30.3 | 33.6 | 29.1 | 30.3 | 19.5 |
| Comp. 11 | Comp. 11 | S-34 | 13.6 | 21.5 | 26.5 | 27.7 | 27.6 | 25.3 | 27.7 | 16.6 |
| Comp. 12 | Comp. 12 | E-88 | 10.0 | 15.4 | 17.3 | 19.3 | 21.6 | 23.1 | 19.3 | 12.1 |

Fig. 7

Table 8

| Embodiment | 20℃/50%RH | | | | | | | | 35℃/85%RH | | | | | | | |
|---|---|---|---|---|---|---|---|---|---|---|---|---|---|---|---|---|
| | Initial stage | | | | 500,000 | | | | Initial stage | | | | 500,000 | | | |
| | Image density | Fog | Resolution | Charge amount | Image density | Fog | Resolution | Charge amount | Image density | Fog | Resolution | Charge amount | Image density | Fog | Resolution | Charge amount |
| 37 | 1.42 | 0.001 | 8.0 | 22.5 | 1.42 | 0.001 | 7.0 | 22.5 | 1.42 | 0.001 | 8.0 | 22.8 | 1.42 | 0.001 | 8.0 | 21.8 |
| 38 | 1.41 | 0.001 | 8.0 | 22.0 | 1.42 | 0.001 | 7.0 | 22.0 | 1.42 | 0.001 | 8.0 | 22.7 | 1.42 | 0.001 | 8.0 | 21.0 |
| 39 | 1.42 | 0.001 | 8.0 | 21.9 | 1.42 | 0.001 | 7.0 | 21.9 | 1.42 | 0.001 | 8.0 | 22.4 | 1.42 | 0.001 | 8.0 | 20.1 |
| 40 | 1.41 | 0.001 | 8.0 | 22.0 | 1.42 | 0.001 | 7.0 | 22.0 | 1.42 | 0.001 | 8.0 | 22.5 | 1.42 | 0.001 | 8.0 | 20.4 |
| 41 | 1.41 | 0.001 | 8.0 | 22.1 | 1.42 | 0.001 | 7.0 | 22.1 | 1.42 | 0.001 | 8.0 | 27.5 | 1.42 | 0.001 | 8.0 | 20.3 |
| 42 | 1.41 | 0.001 | 8.0 | 23.0 | 1.42 | 0.001 | 7.0 | 23.0 | 1.42 | 0.001 | 8.0 | 22.5 | 1.42 | 0.001 | 8.0 | 20.3 |
| 43 | 1.41 | 0.001 | 8.0 | 21.5 | 1.42 | 0.001 | 7.0 | 21.5 | 1.43 | 0.001 | 8.0 | 22.1 | 1.43 | 0.001 | 8.0 | 20.1 |
| 44 | 1.42 | 0.001 | 8.0 | 21.1 | 1.42 | 0.001 | 7.0 | 21.1 | 1.42 | 0.001 | 8.0 | 22.1 | 1.42 | 0.001 | 8.0 | 20.0 |
| 45 | 1.41 | 0.001 | 8.0 | 21.6 | 1.42 | 0.001 | 7.0 | 21.6 | 1.42 | 0.001 | 8.0 | 22.4 | 1.42 | 0.001 | 8.0 | 20.4 |
| 46 | 1.41 | 0.001 | 8.0 | 20.9 | 1.42 | 0.001 | 7.0 | 20.9 | 1.42 | 0.001 | 8.0 | 21.9 | 1.42 | 0.001 | 8.0 | 20.5 |
| 47 | 1.41 | 0.001 | 8.0 | 21.1 | 1.42 | 0.001 | 7.0 | 21.1 | 1.42 | 0.001 | 8.0 | 21.9 | 1.42 | 0.001 | 8.0 | 20.3 |
| 48 | 1.41 | 0.001 | 8.0 | 21.7 | 1.42 | 0.001 | 7.0 | 21.7 | 1.42 | 0.001 | 8.0 | 21.8 | 1.42 | 0.001 | 8.0 | 20.6 |
| Comp.10 | 1.41 | 0.001 | 8.0 | 30.3 | 1.37 | 0.011 | 4.0 | 30.3 | 1.42 | 0.001 | 8.0 | 23.1 | 1.31 | 0.015 | 3.0 | 16.5 |
| Comp.11 | 1.41 | 0.001 | 8.0 | 27.7 | 1.28 | 0.012 | 4.0 | 27.7 | 1.42 | 0.001 | 8.0 | 24.1 | 1.00 | 0.017 | 3.0 | 12.3 |
| Comp.12 | 1.41 | 0.001 | 8.0 | 19.3 | 1.19 | 0.016 | 4.0 | 19.3 | 1.42 | 0.001 | 8.0 | 16.2 | 1.32 | 0.019 | 2.0 | 10.0 |

Fig. 8

CHARGE CONTROL AGENT AND TONER COMPRISING THE SAME

CROSS-REFERENCE TO RELATED APPLICATIONS

This application claims priority to Chinese Patent Application No. 200710051843.4 filed on Apr. 12, 2007, the contents of which are incorporated herein by reference.

BACKGROUND OF THE INVENTION

1. Field of the Invention

The invention is related to a charge control agent, and a toner containing such a charge control agent.

2. Description of the Related Art

Charge control agents mainly comprised of metal complex has been extensively used in various areas, i.e. in the toner used in forming developer for developing an imaging in electrophotographic technology, as a componential material in the making of such toner (e.g. please refer to patent documents: Japanese Pat. Publ. No. 63-61347, Japanese Pat. Publ. No. 2-16916, Japanese Pat. Publ. No. 2002-53539, Japanese Pat. No. 2531957, Japanese Pat. Publ. No. 7-97530).

The metal complex normally used as charge control agent in toners, including generally known azo-metal complex and salicylate-metal complex.

On one hand, in an imaging forming apparatus using electrophotographic technology to form an imaging, it is necessary to heat the toner imaging recorded on a transfer material in order to fix the imaging. In recent years, for the purpose of energy saving, low temperature fixing is preferred.

However, in the chemical structure of azo-metal complex and salicylate-metal complex, the metal ion often tends to detach from the structure. The result is that in the toners using azo-metal complex or salicylate-metal complex as charge control agent, the detached metal ion may bridge with the resin structure which is another ingredient of the toner. This will cause an increase of the softening point of the toner. Thus high quality imaging in low temperature fixing can not be obtained. In addition, when the environment humidity varies, the imaging quality also varies obviously. These are existing problems.

Thus, there were some suggestions to use metal-free chemicals such as calixarene compounds as a charge control agent for toner. Comparing toners using such charge control agent and toners using metal-complex as charge control agent, the charge characteristics of former are not uniform, and the charge amount of toner particles are not evenly dispersed. The toner particles which are not sufficiently charged will cause the dusting and fogging of toner imaging.

SUMMARY OF THE INVENTION

Based on the above mentioned facts, and the advanced research of the inventors of the invention, it is found that the key problems of traditional charge control agent is uneven crystalline size, high moisture absorption, ill dispersion in resin, and high chance of detachment of metal ion from the chemical structure, etc. To solve these problems and after advanced research, the invention is completed. The purpose of the invention is to provide a charge control agent with excellent charge control property.

Other objects of the invention includes providing a toner with excellent chargeability and capable of providing stably imaging with high quality under any environmental conditions.

The charge control agent of the present invention is a tannic acid metal complex consisting of metal atom from divalent to tetravalent and tannic acid as coordination structure. The toner of the present invention at least contains resin, colorant and the invented charge control agent.

In the present invention, the charge control agent consisting of specific tannic acid metal complex has characteristics of uniform crystals, fast tribocharging speed, high TG stability, low Hygroscopicity and good resin compatibility, and thus has excellent charge control characteristic.

EFFECT OF THE PRESENT INVENTION

Research has shown that current popular charge control agents' disadvantages include the size of crystalline is not uniform, moisture absorption is high, dispersion in resin is not good, and the metal ion is easy to disassociate. Targeting at these disadvantages, research has shown that the particular kind of tannic acid metal complex used as charge control agent in the present invention has uniform crystalline size, high tribo charge speed, less hygroscopic, and more compatible with resin, thus results in excellent charge control ability.

The toner in the present invention contains above mentioned charge control agent with excellent charge control ability. So the environmental influence is minimized and it is able to produce high quality imaging. In addition, the excellent charge characteristics reduce the possibility of dusting and fogging of unevenly charged toner particles, thus high quality imaging can be obtained.

Hereafter there is a detailed description of the present invention.

The charge control agents in the present invention is a tannic acid metal complex consisting of metal atom from divalent to tetravalent and tannic acid as coordination structure (hereafter referred to as "particular tannic acid metal complex").

The tannic acid compound in the particular tannic acid metal complex is as the following chemical structure (I), Chemical Structure (I)

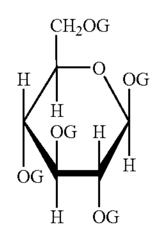

In the structure, G is a group as shown in the following chemical structure (II), Chemical Structure (II)

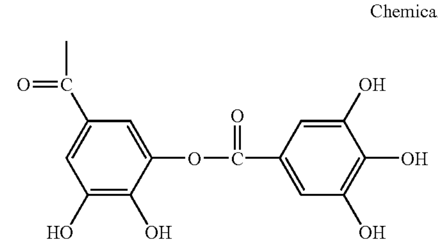

The particular tannic acid metal complex can be formulated as the structure of the following general formula (1), $$[L]M_n \qquad \text{General Formula (1)}$$

In the general formula (1), M stands for metal atom from divalent to tetravalent, and L stands for the coordination structure of tannic acid; n might be 0.5-5.

M group can be a metal atom such as Al, Cr, Zn, Zr, Fe, Co, Ni, and Cu, etc.

In addition, there can be an anti-ion in the structure of the particular tannic acid metal complex.

The anti-ion can be a cation such as K+, H+, NH4+, and Na+, etc.

The preferred examples of the particular tannic acid metal complex (1) including the following compounds:

The charge control agents composed of the particular tannic acid metal complex can be prepared by the following reaction. For example, prepare tannic acid solution by resolving the tannic acid compound in a proper solvent, and prepare a solution containing metal ion. Mix the tannic acid compound solution with the metal ion solution for the purpose of metal coordination in a ratio of 1 mol:2-3 mol. Adjust the PH value of the mixture to 2-11. In detail, at the initial stage of mixing, adjust pH value to weak acid when mixing, and then adjust pH value of the mixture to weak alkaline after mixing. Then heat the mixture to 30-90° C. and mix for 1-48 hours to complete the coordination of metal ion by heating and stirring, and form metal complex. Such is the preparation method to obtain the complex.

The raw tannic acid compound and the metal ion solution used in the preparation of the complex can be selected according to the type of tannic acid metal complex required.

That is, the metal ion solution can be such as zinc chloride solution, ferric trichloride solution, aluminum sulfate solution, chromium sulfate solution, zirconium oxychloride solution, aluminum chloride solution, chromium chloride solution, and ferric chloride solution, etc.

The preferred solvent used to prepare raw tannic acid metal compound solution includes water, methanol, ethanol, n-propanol, isopropanol, glycerine, acetone, and acetic acid.

At the initial stage of mixing of tannic acid solution and metal ion solution, it is better to maintain the pH value of the mixture of tannic acid solution and metal ion solution as weak acid. In details, it is good to maintain pH value at 3, better at 3.5, best at 3.5-6.5, if the pH value is below 3, it will be hard to dissociate the phenolic hydroxyl in tannic acid structure, and solubility will be reduced and reaction is inhibited.

When adjusting pH value at the initial stage of mixing, hydrochloric acid and sulfuric acid can be used as the solvent to form metal ion solution.

During the formation of the complex, it is necessary to ionize the phenol carboxyl group. It's good to maintain the PH value of the solution below 10, better below 9, best at 7.5-9. The weak basic solution facilitates the ionization of the phenol carboxyl group and therefore improves the formation of the complex. During this stage of PH value adjustment, sodium hydroxide, potassium hydroxide, calcium hydroxide and ammonia can be used.

In addition, in the tannic acid solution and metal ion solution, if the organic solvent such as alcohols is used, it is impossible to adjust the PH value during the reaction. Basic materials such as sodium ethylate and kalium ethylate can be used to control the reaction.

Treat the above mentioned reaction resultant of the complex formation process with after-treatment such as washing and drying, and obtain the charge control agent composed of the metal complex from such complex formation process.

Here the washing liquid can be water, methanol, ethanol, glycol, ethyl acetone, n-propanol, isopropanol, glycerine, acetone and acetic acid, etc.

In the above mentioned charge control agent of the present invention, the particular tannic acid metal complex (1) and the particular tannic acid metal complex (2) forming the charge control agent have the following characteristics: high charge speed and high thermo stability, good dispersability, low moisture absorption, and good compatibility with resin. Thus excellent charge control capability is obtained.

In addition, the metal ion coordination in the particular tannic acid complex (1) and particular tannic acid complex (2) is very strong, which minimize the disengagement of metal ions in the metal complex. Thus in the cases where such charge control agents are used in the toner formula, disadvantages caused by the free metal ion impurity which are disengaged from the structure, such as metal bridging between free metal ion and resin which undermines the toner characteristics and the high fluctuation of imaging quality in various environmental humidity, can be minimized.

The above mentioned charge control agent of the present invention can be used as an ingredient of toner as a developer for electrophotography and has very good performance.

In the toner of the present invention which adopts as a necessary ingredient the above mentioned particular tannic acid metal complex as charge control agent, it also contains resin and colorant, and optional additives such as release agent which is used to improve fusing property, and other external additives. These apply to both color and monochrome toner.

The resin ingredients here except charge control agent are not limited, all suitable publicly know materials can be adopted.

In embodiment, the resin used can be thermoplastic resin such as styrene acrylic resin, polyester resin, and epoxy resin. These resins can be use separately or in combination.

The colorants used can be carbon black, magnetic materials, dye, and pigment. Carbon black used can be channel black, furnace black, acetylene black, thermal black, and gas black, etc. The magnetic materials used can be high intensity magnetic materials such as iron, nickel, and cobalt; and compounds of these such as alloy of these metals, ferrite, and magnetite; and metal alloy which does not containing high intensity magnetic metal but can show high magnetism after heat treatment, such as Huesler alloy including manganese-copper-aluminum alloy and manganese-copper-stannum, and chromium dioxide, etc.

Dyes used in the toner can be C. I. solvent red 1, solvent red 49, solvent red 52, solvent red 58, solvent red 63, solvent red 111, solvent red 122; C.I. solvent yellow 19, solvent yellow 44, solvent yellow 77, solvent yellow 79, solvent yellow 81, solvent yellow 82, solvent yellow 93, solvent yellow 98, solvent yellow 103, solvent yellow 104, solvent yellow 112, solvent yellow 162; C.I. solvent blue 25, solvent blue 36, solvent blue 60, solvent blue 70, solvent blue 93, solvent blue 95, etc, or a combination of those. Pigments used in the toner can be C. I. pigment red 5, pigment red 48:1, pigment red 53:1, pigment red 57:1, pigment red 122, pigment red 139, pigment red 144, pigment red 149, pigment red 166, pigment 177, pigment red 178, pigment red 222, pigment red 239; C.I. pigment orange 31, pigment orange 43; C.I. pigment yellow 14, pigment yellow 17, pigment yellow 74, pigment yellow 93, pigment yellow 94, pigment yellow 138, pigment yellow 155, pigment yellow 180, pigment yellow 185; C.I. pigment green 7; C.I. pigment blue 15:3, pigment blue 60, or a combination of those.

The amount of these materials is 2-10% of the total weight of the toner, preferred amount is 3-8%.

The suitable wax that used in the toner of the present invention is selected from hydrocarbon wax, ester wax, natural wax, and amide wax.

Hydrocarbon wax includes low molecular weight polyvinyl wax, low molecular weight polypropylene wax, microcrystalline wax, Fischer-Tropsch wax and paraffin wax.

Ester wax includes ester of higher fatty acid and higher alcohols, e.g. behenyl, behenate, behenyl stearate, stearoyl stearate, pentaerythritol stearate and pentaerythritol behenate, etc.

Natural wax includes carnauba wax, honey wax, ice wax, etc.

These waxes can be use separately or in combination.

The amount of the wax is 2-30% by weight of the total resin particle composition, preferred amount is 3-25%, most preferred amount is 4-20%.

External Additives

For the purpose of increasing fluidity, cleaning property and transfer property, various external additives may be used in the toner of the present invention. The external additives are not explicitly limited. Usable examples include inorganic micro particles, organic micro particles, and lubricant. Examples of inorganic micro particles include silicon dioxide, titanium dioxide, and aluminum oxide. Further, these particles are subject to hydrophobicity-imparting treatment by silane coupling agent or titanium coupling agent. Preferred number average particle size of these inorganic particles is 5-300 nm. The particle size is determined under SEM×50000, using average number of Feret diameter of 500 particles.

The amount of external additives used in the toner can be 0.1-5.0% of total weight, preferably 0.5-4.0% weight. In addition, external additives can use a combination of above mentioned materials.

Further, viewing from the point of transfer property and cleaning property, metal salt of higher fatty acid may also be used, such as zinc stearate, lithium stearate, or calcium stearate, etc. The amount of such additives is 0.01-0.5% by weight.

The amount of charge control agent in the toner of the present invention, is 0.1-3 part by weight of every 100 part weight of the toner including the weight of the charge control agent, the preferred amount is 0.5-2 part.

In toner where the amount ratio of charge control agent is too small, the chargeability of the toner may be insufficient. On the other hand, when the amount ratio of charge control agent is too big, the charge conductivity of the charge control agent will lead to the leak of charge which prohibits the toner from sufficient charging. At the same time, it might contaminate imaging forming device components such as developer roller sleeve, particularly when the toner is used as a part of duel-component developer, where the carrier is polluted so the toner can not obtaining sufficient charge amount.

The preparation method of toner of the present invention is not limited, generally adopted methods such as melting-kneading-pulverization method, suspension polymerization method, emulsion aggregation method and mini-emulsion aggregation method and polyester expand method and other publicly known methods can be used.

When melting-kneading-pulverization method is used in the toner manufacturing, due to the high metal coordination force in the charge control agent of the present invention, the occurrence of metal ion disengagement is rare. The problem of metal ion bridging in the melting-kneading-pulverization method is not happening thus there is no damage to the fusion property. In addition, the charge control agent has excellent dispersability in resin.

In addition, in methods which polymerization reaction is used, the high metal coordination force in the charge control agent prevents the charge control agent from water adding decomposition during dispersion in the aqueous medium, thus minimize the decomposition of the charge control agent. Further, thanks to the existence of metal coordination binding and ion binding, the dispersability of the charge control agent in aqueous medium is good, and easier to form micro particles of charge control agent. In addition, its dispersability in monomer and solvent is good.

The following are records of toner preparation methods.

1) Melting-Kneading-Pulverization Method

In the pulverization method, first dry-mix (premixing) the powder of resin, colorant and the charge control agent of the present invention (and optional release agent if necessary), then use equipment such as twin roller extruder to melt and knead the mixture, after cooling pulverize and classify the mixture and obtain the resultant toner. Pulverization can be either mechanical grinding or jet milling.

2) Emulsion Aggregation and Mini-Emulsion Aggregation Method

Emulsion aggregation method refers to a preparation method in which resin particle, colorant particle and the particle of the charge control agent of the present invention are aggregated and fused to form toner particles. In this method, optional release agent may also be used. In this method, the number average size of the resin particle, colorant particle and the charge control agent particle of the present invention preferably is preferred between 50-200 nm. Directly aggregate monomer particles in an aqueous medium by emulsion aggregation reaction or mini-emulsion aggregation reaction to form toner particles is a preferred method. In such method, uniform particle can be obtained. The dispersion of colorant particles is achieved by mechanically homogenizing the water-colorant mixture with the presence of surfactant. The homogenizer used can be CLEARMIX or bead miller. The charge control agent of the present invention can be dispersed using the same mechanical homogenizer as colorant.

3) Suspension Polymerization Method

This is a method first mix the monomer, colorant and the charge control agent of the present invention (and optional release agent if necessary), and then using mixer to disperse colorant and the charge control agent of the present invention (and optional release agent if necessary) in monomer. Then disperse the mixture in an aqueous medium with disperse stabilizer and form oil drops. After that, initiate the polymerization reaction of the monomer. Remove the disperse stabilizer in the polymerized monomer, and treat it with filtration and drying to obtain toner. In this method, disperse stabilizer is easy to remove. Preferred examples include hardly water-soluble inorganic colloid such as calcium phosphate.

4) Polyester Expand Polymerization Method

Add denatured polyisocyanate, multivalent amine as molecular elongation agent, colorant and the charge control agent of the present invention in a solvent and mix. Optional release agent may also be used. Disperse the disperse liquid in an aqueous medium to form oil drops, and heat the mixture to expand the molecule. Then remove the solvent and control the shape of the particle, filtering and drying to obtain toner.

The above mentioned toner of the present invention can be used as magnetic or non-magnetic mono-component developer, or mix with carrier to use as duel-component developer.

The necessary ingredients of toner are as follows:

In the cases where such toner is used as magnetic monochrome developer, suitable black colorants include magnetite, preferably those number average particle size is between 80-200 nm. The crystalline shape of magnetite can be cubic, spherical, and octahedral. In occasion where a reddish toner is expected, spherical shape magnetite is preferred. In occasion where a bluish toner is expected, cubic shape magnetite is preferred. The amount of magnetic materials used in toner used as magnetic mono-component developer varies as developing method varies. In non-contact developing method, the preferred amount of magnetic material is 35-45% of the total weight of the toner. If the amount used is too small, dusting may occur. On the other hand, over usage of magnetic material may result in inferior developing property.

In occasion where duel-component developer is used, the carrier in such duel-component toner can be selected from iron, ferrite, magnetite, or the alloy of these metals with those publicly know metal such as aluminum or lead. Ferrite is a preferred choice. More preferably the alloy does not contain copper and zinc, but containing light alkali metal or light alkaline earth metal's alloy with ferrite. In addition, when using these metals as the core of carrier, it is preferred to coat with the core with silica resin, styrene acrylic resin, acrylic resin, or resin containing florin. The volume average size of the carrier is 30-100 nm.

The above mentioned toner of the present invention contains charge control agent which provide excellent charge control property. Thus in the very different environments such as high temperature and high humidity, or low temperature and low humidity, a high imaging quality can be ensured. In addition, due to the excellent tribo-charge ability, there is no possibility of dusting and fogging caused by the unevenly charged toner particles. Thus high quality imaging can be obtained.

In such toner, the ion coupling strength in the tannic acid metal complex which is used as charge control agent is very strong, and that prevents the detachment of metal ion which forms the metal complex. So the problems caused by the free metal ion as an impurity content, such as the bridging between metal ion and resin which destroys the toner property, or large variation of the imaging quality under different environments, can be minimized.

Thus the toner of the present invention can provide excellent imaging quality even in low temperature fusing.

BRIEF DESCRIPTION OF THE DRAWINGS

Tables 1-8 show physical characteristics of toners in accordance with various embodiments of the invention.

DETAILED DESCRIPTION OF THE INVENTION

The following are embodiments of the invention, but they should not form a limit to the invention.

Embodiment 1 for Preparing Charge Control Agent

Resolve 63.5 g of zinc chloride in 350 ml of water, and adjust the PH value to 8.0 with 6 mol/L concentration sodium hydroxide solution. Resolve 850 g of tannic acid in 1.2 L of water to form tannic acid solution, and adjust the PH value of this solution to 4.5 with sodium hydroxide and hydrochloric acid, drop the tannic acid solution over 30 minutes into the previous solution, and adjust the PH value to 8.5 with sodium hydroxide. React at 40° C. for 4 hours with substantial stirring. Filter the reaction liquid before cooling down, wash the reaction resultant after filtration with 50% concentration ethanol, then dry and pulverize to obtain powder form metal complex (hereafter referred to as 'charge control agent (1)) 837.5 g.

The resultant charge control agent (1) is a tannic acid metal complex with structure consisting of one zinc as metal atom, and anti-ion is sodium.

Embodiment 2 for Preparing Charge Control Agent

Resolve 30.5 g of ferric trichloride in ethanol containing 1% sodium ethylate, Resolve 850 g of tannic acid in ethanol to form tannic acid solution and drop the tannic acid solution into above solution over 10 minutes. Maintain the temperature of the system at 35° C. and react for 2 hours with substantial stirring. Filter the reaction liquid before cooling down, wash the reaction resultant after filtration with ethanol, then dry and pulverize to obtain powder form metal complex (hereafter referred to as 'charge control agent (2)') 842.0 g.

The resultant charge control agent (2) is a tannic acid metal complex with structure consisting of one ion as metal atom, and anti-ion is sodium

Embodiment 3 for Preparing Charge Control Agent

Resolve 40 g of aluminum sulfate in 300 ml of water, and adjust the PH value of the solution to 3.5 with 5 mol/L concentration sodium hydroxide solution. Resolve 850 g of tannic acid into 0.4 L water to form tannic acid solution and adjust the PH value of this solution to 4.5 with sodium hydroxide and hydrochloric acid. Drop the tannic acid solution into above solution over 30 minutes. Maintain the temperature of the system at 60° C. and react for 16 hours with substantial stirring. Filter the reaction deposit, wash, dry and pulverize to obtain powder form metal complex (hereafter referred to as 'charge control agent (3)') 322 g.

The resultant charge control agent (3) is a tannic acid metal complex with structure consisting of one aluminium as metal atom, and anti-ion is sodium

Embodiment 4 for Preparing Charge Control Agent

Resolve 38 g of chromium sulfate in 200 ml of water, and adjust the PH value of the solution to 9.0 with 4 mol/L concentration sodium hydroxide solution. Resolve 1000 g of tannic acid into 2 L water to form tannic acid solution and adjust the PH value of this solution to 4.5 with sodium hydroxide and hydrochloric acid. Drop the tannic acid solution into above. solution over 30 minutes. Maintain the temperature of the system at 60° C. and react for 16 hours with substantial stirring. Filter the reaction deposit, wash, dry and pulverize to obtain powder form metal complex (hereafter referred to as 'charge control agent (4)') 993.5 g.

The resultant charge control agent (4) is a tannic acid metal complex with structure consisting of one chromium as metal atom, and anti-ion is sodium

Embodiment 5 for Preparing Charge Control Agent

Resolve 35 g of zirconium oxychloride in 100 ml of water, and adjust the PH value of the solution to 11.0 with 6 mol/L concentration sodium hydroxide solution. Resolve 350 g of tannic acid into 1 L water to form tannic acid solution and adjust the PH value of this solution to 4.5 with sodium hydroxide and hydrochloric acid. Drop the tannic acid solution into above. solution over 30 minutes. Maintain the temperature of the system at 70° C. and react for 12 hours with substantial stirring. Filter the reaction deposit, wash, dry and pulverize to obtain powder form metal complex (hereafter referred to as 'charge control agent (5)') 56 g.

The resultant charge control agent (5) is a tannic acid metal complex with structure consisting of one zirconium as metal atom, and anti-ion is sodium

Embodiment 6 for Preparing Charge Control Agent

Resolve 28 g of aluminum chloride in 50 ml of water, and adjust the PH value of the solution to 3.5 with 12 mol/L concentration sodium hydroxide solution. Resolve 350 g of tannic acid into water to form tannic acid solution and adjust the PH value of this solution to 4.5 with sodium hydroxide and hydrochloric acid. Drop the tannic acid solution into above. solution over 30 minutes. Maintain the temperature of the system at 60° C. and react for 24 hours with substantial stirring. Filter the reaction deposit, wash, dry and pulverize to obtain powder form metal complex (hereafter referred to as 'charge control agent (6)') 327 g.

The resultant charge control agent (6) is a tannic acid metal complex with structure consisting of two aluminiums as metal atoms, and anti-ion is sodium Embodiment 7 for Preparing Charge Control Agent Resolve 75 g of aluminum sulfate into water to form a concentration of 15 mol/L solution, and adjust the PH value of the solution to 3.5 with 7 mol/L concentration sodium hydroxide solution. Resolve 170 g of tannic acid into ethanol to form 0.2 mol/L tannic acid solution. Drop the tannic acid solution into above solution. Maintain the temperature of the system at 45° C. and the PH value at 11, react for 28 hours with substantial stirring. Filter the reaction deposit, wash, dry and pulverize to obtain powder form metal complex (hereafter referred to as 'charge control agent (7)') 162 g.

The resultant charge control agent (7) is a tannic acid metal complex with structure consisting of three aluminiums as metal atoms, and anti-ion is sodium.

Embodiment 8 for Preparing Charge Control Agent

Resolve 25 g of aluminum sulfate in water to form a concentration of 5 mol/L solution, and adjust the PH value of the solution to 3.0-3.5 with 6 mol/L concentration ammonia solution. Resolve 175 g of tannic acid into methanol to form 3 mol/L tannic acid solution. Drop the tannic acid solution into above solution. Maintain the temperature of the system at 30° C. and the PH value at 11.0 with sodium hydroxide, react for 18 hours with substantial stirring. Filter the reaction deposit, wash, dry and pulverize to obtain powder form metal complex (hereafter referred to as 'charge control agent (8)') 159 g.

The resultant charge control agent (8) is a tannic acid metal complex with structure consisting of one aluminium as metal atom, and anti-ion is sodium Embodiment 9 for Preparing Charge Control Agent Prepare 2013 g of tannic acid and dissolve it into water to get 3 mol/L tannic acid liquid. Resolve 61 g of zinc chloride in water to form a concentration of 7 mol/L solution, and adjust the PH value of the solution to 7.5 with urea. Drop into this solution the tannic acid solution. Maintain the temperature of the system at 30° C., and the PH value at 11.0 with sodium hydroxide, react for 18 hours with substantial stirring. Filter the reaction deposit, wash, dry and pulverize to obtain powder form metal complex (hereafter referred to as 'charge control agent (9)') 1892 g.

The metal atom which contains in the charge control agent (9) is tannic acid metal complex with 1 zinc atom, antiparticle contains in this charge control agent (9) is sodium ion Embodiment 10 for Preparing Charge Control Agent Resolve 33 g of ferric chloride in water to form a concentration of 4 mol/L solution, and adjust the PH value of the solution to 5.5 with urea. Resolve 2013 g of tannic acid into water to form 3 mol/L tannic acid solution. Drop the tannic acid solution into above solution. Maintain the temperature of the system at 45° C., and the PH value at 11.0 with sodium hydroxide, react for 48 hours with substantial stirring. Filter the reaction deposit, wash, dry and pulverize to obtain powder form metal complex (hereafter referred to as 'charge control agent (10)') 638 g.

The resultant charge control agent (10) is a tannic acid metal complex with structure consisting of one ion as metal atom, and anti-ion is sodium Embodiment 1 for Preparing Charge Control Agent Resolve 32.5 g of ferric chloride in ethanol to form a concentration of 5 mol/L solution, and adjust the PH value of the solution to 6.0 with ethanol containing 5 mol/L sodium ethylate. Resolve 650 g of tannic acid into ethanol to form 3 mol/L tannic acid solution. Drop the tannic acid solution into above solution. Maintain the temperature of the system at 60° C., and the PH value at 11.0 with sodium hydroxide, react for 16 hours with substantial stirring. Filter the reaction deposit, wash, dry and pulverize to obtain powder form metal complex (hereafter referred to as 'charge control agent (11)') 641.5 g.

The resultant charge control agent (11) is a tannic acid metal complex with structure consisting of one ion as metal atom, and anti-ion is sodium Embodiment 12 for Preparing Charge Control Agent Resolve 23 g of aluminum sulfate in ethanol to form a concentration of 5 mol/L solution. Resolve 162 g of tannic acid into 100 ml methanol with 1% sodium ethylate to form 3 mol/L tannic acid solution. Drop the tannic acid solution into above solution. Maintain the temperature of the system at 70° C., and the PH value at 11.0 with sodium hydroxide, react for 6 hours with substantial stirring. Filter the reaction deposit, wash, dry and pulverize to obtain powder form metal complex (hereafter referred to as 'charge control agent (12)') 153 g.

The resultant charge control agent (12) is a tannic acid metal complex with structure consisting of one aluminium as metal atom, and anti-ion is sodium Use the charge control agents obtained from the preparation example 1-example 12 to produce toners, and use thus obtained toners to produce developers.

Example 1 for Preparing Pulverized Toner

Mix 1 part of charge control agent (1), 100 parts of styrene-acrylic resin (styrene:butyl acrylate:methyl methacrylate=70:20:5 (by weight), softening point is 128° C.), 8 parts of carbon black 'MOGUL L' (manufactured by Cabot. Co) and 6 parts of low molecular weight polypropylene '660P' (manufactured by Sanyo Chemical) in a Henschel mixer. Melt and knead the resultant mixture with twin-screw extruder, after cooling down, pulverize with a jet mill and classify with cyclone classifier, to obtain colored particles with a volume average diameter about 8.5 μm.

Then add 0.8 parts of 67% hydrophobic silica dioxide which number average diameter is 12 nm into every 100 parts of the colored particles. Mix with a Henschel mixer to obtain the toner.

Examples 2-12 of Preparation of Pulverized Toner and Comparative Examples 1-3 of Preparation of Pulverized Toner In the examples 1 of preparation of pulverized toner, the charge control agent (1) is replaced by the charge control agent showing in the below Table 1 and the other conditions are kept the same with Example 1 to obtain toner.

Pulverized toners named Toner (1)-Toner (12) using charge control agent (1)-(12) is shown in the below Table 1. In addition, comparative toners named Comparative Toner (1)-Comparative Toner (3) use comparative charge control agents of chromium salicylate [E-81] (made by orient chem.), ring aromatic derivative [E-88] (made by orient chem) and chromium azo complex [S-34] (made by orient chem.) respectively.

Example 1 for Suspension Polymerization Toner

Mix 1 part of charge control agent, 75 part of styrene monomer, 25 part of acrylic butyl ester, 5 part of carbon black (MOGUL L), 3 part of phthalocyanine (P.B. 15:3) and 2 part of bisazo (Isoamyl nitrile). Obtain polymerizing monomer components by good dispersion by sand mill at a rotation speed at 10000 rpm for 30 minutes.

Then add 600 part of ion exchanged water and 500 part of 0.1 mol/L sodium phosphate ($Na3PO4$) in a 2 L four-inlet flask equipped with high rotation speed TK type homogenizer (made for particular mechanical chemical industry) and baffle. Adjust the rotation speed to 12000 rpm and increase temperature to 65° C. Then slowly add 70 part of 1.0 mol/L calcium chloride ($CaCl2$) to prepare water dispersion media containing tiny insoluble calcium phosphate ($Ca3(PO4)2$) as dispersion stabilizer.

Then add polymerizing monomer components into above-mentioned water dispersion media and stir it for 15 minutes at a high rotation speed of 12000 rpm at inner temperature of 65° C. in nitrogen atmosphere to granulate such polymerizing monomer components. After that, change stirrer to spiral mixing leaves to complete polymerization process through the control of rotation speed of spiral leaves and the angle of baffles at same temperature for 10 hours. Cool such suspension liquid after polymerization. Then get rid of dispersion stabilizer by adding hydrochloric acid and wash it many times with water to obtain colorant particles at a volume basis median diameter of 8.2 μm.

After that, add 0.8 part of 67 hydrophobic degree silicon dioxide into 100 part of colorant particles obtained from above and mix them by henschel mixer to obtain toners.

Examples 2-12 of Preparation of Suspension Polymerization Toner and Comparative Examples 1-3 of Preparation of Suspension Polymerization In the example 1 of preparation of suspension polymerization toner, the charge control agent (1) is replaced by the charge control agent showing in the below Table 3 and the other conditions are kept the same with Example 1 to obtain toner.

Suspension polymerization toners named Toner (13)-Toner (24) using charge control agent (1)-(12) is shown in the below Table 5. In addition, comparative toners named Comparative Toner (4)-Comparative Toner (6) use comparative charge control agents of chromium salicylate [E-81] (made by orient chem.) ring aromatic derivative [E-88] (made by orient chem) and chromium azo complex [S-34] (made by orient chem.) respectively.

Example 1 for Preparing Toner with Emulsion Aggregation Method

Prepare Resin Particle Dispersion Liquid

Add into a reactor with stirring device, temperature sensor, cooling tube and nitrogen injector a solution of 16 parts of Sodium lauryl sulphate in 1500 parts of ion exchanged water. Under nitrogen gas current stir at 230 rpm, and heat the system to 80° C. Then, add a solution of 5 parts of potassium sulfate in 100 parts of ion exchanged water into the system, heat the system again to 80° C. In one hour drop into the reactor a polymerizable monomer liquid which contains 350 parts of styrene, 125 parts of n-butylacrylate, 25 parts of methacrylic acid and 4 parts of n-dodecanethiol. Heat to 80° C. for 2 hours, and mix to polymerize, to prepare resin particle disperse liquid (1).

Use the electrophoresis light scattering photometer (ELS-800) (Otsuka electron company) to determine the particle size in the resin particle disperse liquid (1), the volume average diameter of which is 110 nm.

Prepare Carbon Black Disperse Liquid

Resolve 10 parts of Sodium lauryl sulphate in 160 parts of ion exchanged water. Slowly add 40 parts of carbon black 'MOGUL L' (manufactured by CABOT, CO.) into the solution, disperse with 'CLEARMIX' (manufactured by M Technique CO.), to prepare colorant dispersion liquid (1).

Use the electrophoresis light scattering photometer (ELS-800) (Otsuka electron company) to determine the particle size in the colorant dispersion liquid (1), the volume average diameter of which is 120 nm.

Prepare Charge Control Agent Disperse Liquid

Resolve 5 parts of Sodium lauryl sulphate in 200 parts of ion exchanged water. Slowly add 5 parts of charge control agent (1) into the solution. Disperse with sand mill to prepare a charge control agent disperse liquid (1).

Use the electrophoresis light scattering photometer (ELS-800) (Otsuka electron company) to determine the particle size of charge control agent disperse liquid (1) is 110 nm.

Prepare Release Agent Disperse Liquid

Heat the solution of 6 parts of sodium sulfate in 200 parts of ion exchanged water to 90° C., while stirring, slowly add 40 parts of melted 90° C. carnauba wax, treat with sonication to disperse and form wax disperse liquid. Use the electrophoresis light scattering photometer (ELS-800) (Otsuka electron company) to determine the particle size is 130 nm.

Aggregate Confection Toner

Add into a reactor with stirring device, temperature sensor, cooling tube and nitrogen injector the above mentioned resin particle disperse liquid (1), colorant disperse liquid (1), charge control agent disperse liquid (1), release agent disperse agent (1) and 1400 parts of ion exchanged water, and add into this mixture a solution of 10 parts of polyoxyethylene-2-sodium dodecylsulfate ether in 500 parts of ion exchanged water. Adjust the temperature of the system to 30° C., and adjust the PH value to 10 with 5N sodium hydroxide water solution.

Then resolve 100 parts of magnesium chloride in 100 parts of ion exchanged water and add into the mixture at 30° C. during 10 minutes under continuous stirring. Keep stirring for further 3 minutes and heat the system to 90° C. over 60 minutes. Keep the temperature at 90° C. to let the particles aggregate. Use 'Coulter Multilizer III to determine the size of aggregated particle. When the desired particle size is obtained, add a solution of 300 parts of sodium chloride in 1000 parts of ion exchanged water to stop particle growth. Heat the mixture to 98° C. to let the particle fuse until test with 'FPIA-2100' the average roundness of the particles is 0.965. Cool the liquid to 30° C., adjust the PH value to 4.0 with hydrochloric acid, and stop stirring.

Examples 2-12 of Preparation of Emulsion Aggregation Toner and Comparative Examples 1-3 of Preparation of Emulsion Aggregation Toner In the preparation example 1 of emulsion aggregation toner, to obtain toner by replacing charge control agent (1)

with charge control agents in Table 5, other conditions remain the same as preparation example 1 of emulsion aggregation toner 1.

Emulsion aggregation toners named Toner (25)-Toner (36) using charge control agent (1)-(12) is shown in the below Table 5. In addition, comparative toners named Comparative Toner (7)-Comparative Toner (9) use comparative charge control agents of chromium salicylate [E-81] (made by orient chem.), ring aromatic derivative [E-88] (made by orient chem) and chromium azo complex [S-34] (made by orient chem.) respectively.

Example 1 for Preparing Toner with Polyester Expand Polymerization Method

Example of Preparing Denatured Polyisocyanate

Add into a reactor with mixing and nitrogen injection device 724 parts of bisphAlkenyl A ethylene oxide 2 mol additive, 200 parts of isophthalic acid, 70 parts of fumaric acid, and 2 parts of dibutylin oxide. React under 230° C. and normal pressure (one atmospheric pressure) for 8 hours, and under 12 mm Hg for 5 hours. Cool the system to 160° C., add 32 parts of phthalic anhydride, react for 2 hours to obtain polyester [a1]. The unformed polyester [a1] has a glass transition point of 59° C., and a softening point of 121° C., the number average molecular weight (Mn) is 6,000, and the weight average molecular weight (Mw) is 28,000.

Then add to every 1,000 parts of the unformed polyester [a1] 2,000 parts of ethyl acetate, and 120 parts of isophorone diisocyanate. React at 80° C. for 2 hours and obtain denatured polyisocyanate [1].

Put in a reactor with hydraulic seal and stirrer 450 parts of ethyl acetate, 300 parts of denatured polyisocyanate [1], 14 parts of isophoronediamine, 4 parts of copper phthalocyanine blue, 4 parts of carbon black, 15 parts of carnauba wax, 3 parts of charge control agent, and react under 20° C. for 2 hours to obtain toner composite [1].

At the same time, Put into another reactor 600 parts of ion exchanged water, 60 parts of methyl ethyl ketone, 60 parts of tricalcium phosphate, 0.3 parts of Sodium dodecyl benzene sulfonate. Stir with TK homogenizer (Primix Corporation) at 15,000 rpm under 30° C. for 3 minutes. Add this mixture to the aqueous dispersion liquid of the above mentioned toner composite [1], heat to 80° C., and treat with urea for 10 hours to obtain particles with a volume average diameter of 5.5 μm.

Move the urea-treated toner composite [1] to another mixer, add 0.3 parts of sodium dodecylsulfate under 30° C., and heat to 50° C. to react for 3 hours to let the particle surface coalescent with dodecyl group. Then rapidly heat up to 80° C. to remove ethyl acetate. Cool the system to room temperature until ethyl acetate is completely removed; add 150 parts of 35% thick hydrochloric acid to resolve the tricalcium phosphate on the surface of the toner particles.

Separate the liquid and the solid, disperse in ion exchange water the dehydrated toner press cake. Repeat this separation process for 3 times, wash and dry under 40° C. for 24 hours, to obtain toner particle.

Examples 2-12 of Preparation of Polyester Expand Polymerization Toner and Comparative Examples 1-3 of Preparation of Polyester Expand Polymerization Toner In the preparation example 1 of polyester expand polymerization toner, to obtain toner by replacing charge control agent (1) with charge control agents in Table 7, other conditions remain the same as preparation example 1 of polyester expand polymerization toner 1.

Then, name the polyester expand polymerization toners using the charge control agent (2)-charge control agent (12) as toner (37)-toner (48). And name the toner using comparative charge control agent chromium salicylate [E81] (Orient Chemical produce), calixarenes derivative [E-88] (Orient) and Chromium-Azo Complex [S34] (Orient Chemical produce) comparative charge control agent (3) as comparative toner (10)-comparative toner (12).

Embodiment 1-48 and Comparative Embodiment 1-12

Mix the toners with carrier comprised of light metal ferrite coated with silicone and the volume average size of which is 65 μm, to obtain developers containing 8% toner.

Then name the duel-component developers using toner (1)-toner (48) as developer (1)-developer (48). And name the duel-component developers using comparative toner (1)-comparative toner (12) as comparative developer (1)-comparative developer (12).

Use the following method to evaluate the developer (1)-developer (48) and comparative developer (1)-comparative developer (12). The result is as follows:

(1) Charge Characteristics

Weigh 1 g of the each kind of toners which are used to produce developer (1)-developer (116) and comparative developer (1)-comparative developer (12), separately put into a 20 ml glass test-tube with 10 g of carrier. Under 20° C. and 50% humidity RH environment, stir with YAYOI (YAYOI is a company name) shaker for 1 minute, 2 minutes, 5 minutes, 10 minutes 20 minutes and 60 minutes. Under normal temperature and normal humidity, test with TB-200 charge amount testing apparatus (manufactured by Toshiba, Co.) to determine the charge amounts.

(2) Charge Stabilization Property

Weigh 1 g of the each kind of toners which are used to produce developer (1)-developer (116) and comparative developer (1)-comparative developer (12), separately put into a 20 ml glass test-tube with 10 g of carrier. Under normal temperature (20° C.) and normal humidity (45%-75%), test with TB-200 charge amount testing apparatus (manufactured by Toshiba, Co.) to determine the charge amounts (show in table 1 as initial charge amount). Then store in 35° C. and 85% humidity RH environment for 24 hours, test the charge amount again (show in table 1 as charge amount after storage).

(3) Imaging Quality

By contact imaging method and using respectively developer (1)-developer (116) and comparative developer (1) and comparative developer (12), in a photocopier (Ricoh Imagio Neo 1050Pro) which has a maximum speed of 105 ppm, under 20° C. and 50% humidity RH environment, as well as 35° C. and 85% humidity RH environment, to produce imaging of A4 size and a coverage of 5%. The imaging copying mode is using A4 photocopy paper and pause for 1 minute after every 50 pages, for a total 500,000 pages. Test with 'RD-918' of Macbeth company the imaging density the black imaging of the initial imaging (show in table 2, 4 and table 6 as 'initial') and the $500,000^{th}$ imaging (show in table 2, 4 and table 6 as '$500,000^{th}$'), and the fog density of blank space in these pages. The tests are conducted regarding the reflecting rate of the copying paper as '0', and to determine the relative reflect rate of the imaging.

In addition, observe the character resolution with a 10× magnifier on the initial imaging and the $500,000^{th}$ imaging.

While observe with eyes, test the toner charge amount after the initial imaging and after the 500,000$^{th}$ imaging.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A toner comprising a resin, a colorant, and a charge control agent, said charge control agent comprising a metal tannic acid complex and said charge control agent being a separate chemical entity from said colorant.

2. The toner of claim 1, wherein said resin is a thermoplastic resin selected from styrene acrylic resin, polyester resin, an epoxy resin, or a combination thereof.

3. The toner of claim 2, wherein said resin is a styrene-butyl acrylate-methyl methacrylate resin.

4. The toner of claim 3, wherein the colorant is a carbon black, a magnetic material, a dye, or a pigment;

the carbon black is channel black, furnace black, acetylene black, thermal black, or gas black;

the magnetic material is a high intensity magnetic material selected from iron, nickel, cobalt, or a compound comprising thereof selected from ferrite or magnetite; a metal alloy which does not comprise a high intensity magnetic metal but exhibits magnetic properties after heat treatment selected from a Huesler alloy, a manganese-copper-aluminum alloy, a manganese-copper-tin alloy, or chromium dioxide;

the dye is solvent red 1, solvent red 49, solvent red 52, solvent red 58, solvent red 63, solvent red 111, solvent red 122; solvent yellow 19, solvent yellow 44, solvent yellow 77, solvent yellow 79, solvent yellow 81, solvent yellow 82, solvent yellow 93, solvent yellow 98, solvent yellow 103, solvent yellow 104, solvent yellow 112, solvent yellow 162; solvent blue 25, solvent blue 36, solvent blue 60, solvent blue 70, solvent blue 93, solvent blue 95, or a combination of thereof;

the pigment is pigment red 5, pigment red 48:2, pigment red 53:1, pigment red 57:1, pigment red 122, pigment red 139, pigment red 144, pigment red 149, pigment red 166, pigment 177, pigment red 178, pigment red 222, pigment red 239; pigment orange 31, pigment orange 43; pigment yellow 14, pigment yellow 17, pigment yellow 74, pigment yellow 93, pigment yellow 94, pigment yellow 138, pigment yellow 155, pigment yellow 180, pigment yellow 185; pigment green 7; pigment blue 15:3, pigment blue 60, or a combination thereof; and the charge control agent is zinc tannate, ferric tannate, aluminum tannate, or chromium tannate.

5. The toner of claim 1, wherein said colorant is a carbon black, a magnetic material, a dye, or a pigment.

6. The toner of claim 5, wherein said carbon black is channel black, furnace black, acetylene black, thermal black, or gas black.

7. The toner of claim 5, wherein the magnetic material is a high intensity magnetic material selected from iron, nickel, cobalt, or a compound comprising thereof selected from ferrite or magnetite; a metal alloy which does not comprise a high intensity magnetic metal but exhibits magnetic properties after heat treatment selected from a Huesler alloy, a manganese-copper-aluminum alloy, a manganese-copper-tin alloy, or chromium dioxide.

8. The toner of claim 5, wherein the dye is solvent red 1, solvent red 49, solvent red 52, solvent red 58, solvent red 63, solvent red 111, solvent red 122; solvent yellow 19, solvent yellow 44, solvent yellow 77, solvent yellow 79, solvent yellow 81, solvent yellow 82, solvent yellow 93, solvent yellow 98, solvent yellow 103, solvent yellow 104, solvent yellow 112, solvent yellow 162; solvent blue 25, solvent blue 36, solvent blue 60, solvent blue 70, solvent blue 93, solvent blue 95, or a combination of thereof.

9. The toner of claim 5, wherein the pigment is pigment red 5, pigment red 48:2, pigment red 53:1, pigment red 57:1, pigment red 122, pigment red 139, pigment red 144, pigment red 149, pigment red 166, pigment 177, pigment red 178, pigment red 222, pigment red 239; pigment orange 31, pigment orange 43; pigment yellow 14, pigment yellow 17, pigment yellow 74, pigment yellow 93, pigment yellow 94, pigment yellow 138, pigment yellow 155, pigment yellow 180, pigment yellow 185; pigment green 7; pigment blue 15:3, pigment blue 60, or a combination thereof.

10. The toner of claim 1, wherein the metal tannic acid complex comprises aluminum, chromium, zinc, zirconium, iron, cobalt, nickel, or copper.

11. The toner of claim 1, wherein the charge control agent comprises potassium ions, hydrogen ions, ammonium ions, or sodium ions.

12. The tonner of claim 1, wherein the charge control agent is zinc tannate.

13. The tonner of claim 1, wherein the charge control agent is ferric tannate.

14. The tonner of claim 1, wherein the charge control agent is aluminum tannate.

15. The tonner of claim 1, wherein the charge control agent is chromium tannate.

16. The toner of claim 2, wherein said charge control agent improves charge distribution characteristics of said colorant.

17. A toner consisting of a resin, a colorant, and a metal tannic acid complex, said colorant being a separate chemical entity from said metal tannic acid complex.

18. The toner of claim 17, wherein said charge control agent is zinc tannate, ferric tannate, aluminum tannate, or chromium tannate.

19. A method for producing a tonner having improved charge transfer properties comprising mixing a charge control agent, said charge control agent comprising a metal tannic acid complex with a resin and a colorant.

20. The method of claim 19, wherein the resin is a thermoplastic resin selected from styrene acrylic resin, polyester resin, an epoxy resin, or a combination thereof;

the colorant is a carbon black, a magnetic material, a dye, or a pigment;

the carbon black is channel black, furnace black, acetylene black, thermal black, or gas black;

the magnetic material is a high intensity magnetic material selected from iron, nickel, cobalt, or a compound comprising thereof selected from ferrite or magnetite; a metal alloy which does not comprise a high intensity magnetic metal but exhibits magnetic properties after heat treatment selected from a Huesler alloy, a manganese-copper-aluminum alloy, a manganese-copper-tin alloy, or chromium dioxide;

the dye is solvent red 1, solvent red 49, solvent red 52, solvent red 58, solvent red 63, solvent red 111, solvent red 122; solvent yellow 19, solvent yellow 44, solvent yellow 77, solvent yellow 79, solvent yellow 81, solvent yellow 82, solvent yellow 93, solvent yellow 98, solvent yellow 103, solvent yellow 104, solvent yellow 112, solvent yellow 162; solvent blue 25, solvent blue 36, solvent blue 60, solvent blue 70, solvent blue 93, solvent blue 95, or a combination of thereof;

the pigment is pigment red 5, pigment red 48:2, pigment red 53:1, pigment red 57:1, pigment red 122, pigment red 139, pigment red 144, pigment red 149, pigment red 166, pigment 177, pigment red 178, pigment red 222, pigment red 239; pigment orange 31, pigment orange 43; pigment yellow 14, pigment yellow 17, pigment yellow 74, pigment yellow 93, pigment yellow 94, pigment yellow 138, pigment yellow 155, pigment yellow 180, pigment yellow 185; pigment green 7; pigment blue 15:3, pigment blue 60, or a combination thereof; and the charge control agent is zinc tannate, ferric tannate, aluminum tannate, or chromium tannate.

* * * * *